US008758990B2

(12) United States Patent
Shah et al.

(10) Patent No.: US 8,758,990 B2
(45) Date of Patent: Jun. 24, 2014

(54) **METHODS FOR DETECTING AND DIFFERENTIATING *MYCOBACTERIUM* GENUS AND *MYCOBACTERIUM AVIUM* COMPLEX IN A SAMPLE OR CULTURE**

(75) Inventors: Jyotsna S. Shah, Santa Clara, CA (US); Helena Weltman, Los Altos, CA (US)

(73) Assignee: ID-Fish Technology, Inc., Santa Clara, CA (US)

( * ) Notice: Subject to any disclaimer, the term of this patent is extended or adjusted under 35 U.S.C. 154(b) by 1351 days.

(21) Appl. No.: 11/975,306

(22) Filed: Oct. 18, 2007

(65) Prior Publication Data

US 2009/0130673 A1    May 21, 2009

Related U.S. Application Data

(63) Continuation-in-part of application No. 11/494,430, filed on Jul. 27, 2006, now Pat. No. 8,632,963.

(60) Provisional application No. 60/703,329, filed on Jul. 28, 2005.

(51) Int. Cl.
| | |
|---|---|
| *C12Q 1/00* | (2006.01) |
| *C12M 1/33* | (2006.01) |
| *C12M 1/00* | (2006.01) |
| *C07H 21/02* | (2006.01) |
| *A01N 47/00* | (2006.01) |
| *B01D 19/00* | (2006.01) |

(52) U.S. Cl.
USPC .......... 435/4; 435/6.1; 435/306.1; 435/5; 435/6.12; 435/307.1; 252/188.2; 514/515

(58) Field of Classification Search
None
See application file for complete search history.

(56) References Cited

U.S. PATENT DOCUMENTS

| | | | |
|---|---|---|---|
| 5,422,277 A | 6/1995 | Connelly et al. | |
| 5,521,300 A | 5/1996 | Shah et al. | |
| 5,597,688 A | 1/1997 | Connelly et al. | |
| 5,629,156 A | 5/1997 | Shah et al. | |
| 6,165,723 A | 12/2000 | Shah et al. | |
| 6,538,107 B1 * | 3/2003 | Hinuma et al. | 530/350 |
| 6,835,393 B2 | 12/2004 | Hoffman et al. | |
| 7,307,103 B2 * | 12/2007 | Prusiner et al. | 514/557 |
| 2004/0224348 A1 | 11/2004 | Brentano et al. | |
| 2005/0059054 A1 * | 3/2005 | Conrad et al. | 435/6 |
| 2007/0042358 A1 | 2/2007 | Shah et al. | |

FOREIGN PATENT DOCUMENTS

WO    2006029014 A2    3/2006

OTHER PUBLICATIONS

St. Amand et al in "Use of Specific rRNA Oligonucleotide Probes for Microscopic Detection of *Mycobacterium avium* Complex Organisms in Tissue" (Journal of Clinical Microbiology, Apr. 2005, pp. 1505-1514).*

* cited by examiner

*Primary Examiner* — Catherine Hibbert
(74) *Attorney, Agent, or Firm* — Pierce Atwood LLP; Kevin M. Farrell; David J. Wilson

(57) ABSTRACT

The present invention relates to compositions and methods for detecting Mycobacterium genus (*Mycobacterium* sp.) bacteria (e.g., *M. tuberculosis*) and *M. avium* complex (MAC; *M. avium, M. scrofulaceum* and *M. intracellulaire*) in a clinical sample or culture. The present invention also relates to differentiating cultures or samples comprising (*Mycobacterium sp.*) bacteria (e.g., *M. tuberculosis*) from cultures or samples comprising *M. avium* complex (MAC; *M. avium, M. scrofulaceum* and *M. intracellulaire*).

46 Claims, No Drawings

METHODS FOR DETECTING AND DIFFERENTIATING *MYCOBACTERIUM* GENUS AND *MYCOBACTERIUM AVIUM* COMPLEX IN A SAMPLE OR CULTURE

FIELD OF THE INVENTION

The present invention relates to compositions and methods for improving cell permeability to foreign particles including the probes of the present invention. The present invention also relates to compositions and methods for detecting *Mycobacterium* genus (*Mycobacterium* sp.) bacteria [e.g., *M. tuberculosis* ] and *M. avium* complex (MAC; *M. avium, M. scrofulaceum* and *M. intracellulaire*) in a clinical sample or culture. The present invention also relates to differentiating cultures or samples comprising (*Mycobacterium* sp.) bacteria (e.g., *M. tuberculosis*) from cultures or samples comprising *M. avium* complex (MAC; *M. avium, M. scrofulaceum* and *M. intracellulaire*).

BACKGROUND

Cells are the basic unit of all living organisms. The one common attribute of almost all cells is that they are surrounded (or bounded) by a cytoplasmic membrane. This membrane harbors the internal contents of the cell and regulates the movement of substances into and out of the cell. Only those molecules that can diffuse across the membrane or are transported across it can move into and out of the cell. Some can pass through the lipid core of the membrane, but others must pass through pores. Still other molecules must cross the membrane attached to carriers in an energy dependent manner. Likewise, the nucleus and other cellular organelles have membranes to regulate the flow of molecules into and out of the organelle.

Fixation is a chemical process that "sets" cellular molecules in place so that the cell or tissue can then be studied. Most agents that are used as fixatives (e.g., alcohols such as ethanol and aldehydes such as paraformaldehyde) work by crosslinking cellular molecules, especially proteins. This crosslinking process prevents the degradation of the cellular structure. Various fixatives are better suited for the preservation of different cellular molecules and structures or for different detection methods. The fixative chosen for any particular purpose will be determined by the nature of that purpose.

Unfortunately, the current methods of fixation often hamper the subsequent ability of a researcher or clinician to detect internal cellular components. In other words, the very thing that prevents the degradation of the cell, fixation, can also set up a barrier to the many types of research and diagnosis that rely on larger sized detection molecules. Because of this, efforts have been made to permeabilize cells or make channels after fixation.

Current methods of permeabilizing the cell membrane after fixation are either i) not effective for all specimens, ii) are too rigorous (thus, destroying the structures to be studied) and/or iii) require expensive equipment. For example, Hoffman, et al., (U.S. Pat. No. 6,835,393) discloses the use of polycarboxylic acid polymers and pH for disrupting cell membranes but this technique can only be used on non-fixed samples. Connelly, et al., (U.S. Pat. Nos. 5,597,688 and 5,422,277) disclose the use of a composition with 2,4-dinitrobenzene sulfonic acid, 2,4-dinitrobenzoic acid or 2,4-dinitrophenol for both cell membrane fixation and permeabilization but these compositions limit the researcher's or clinician's choice of fixative and, thus, limits necessary assay flexibility. Mechanical methods such as sonication, electroporation, etc. usually only work on unfixed samples and require expensive equipment.

Furthermore, the available research and diagnostic methods of the prior art for many cellular targets such as pathologies depends on microscopic evaluations, cellular morphological parameters, staining characteristics and the presence or absence of certain targets. However, many of these diagnostic methods are not entirely accurate or sufficiently sensitive in part due to the difficulty in delivering probes to inside the cell.

*Mycobacterium* has a thick mycolate-rich cell wall (outer covering) which functions as an exceptionally efficient barrier. Within the cell wall is the cytoplasmic membrane. Therefore, it is very difficult to access or release nucleic acids or other cell components within the cytoplasm of the organism using standard procedures (lysis with detergents such as SDS, IGEPAL etc). Therefore, nucleic acids or internal components of the mycobacterium cell cannot be easily detected and analyzed by standard methodology such as in situ hybridization, immunofluorescence or other techniques known in the art whether the sample is from a cell culture or from patient specimen.

The one common attribute of almost all cells (including *Mycobacterium* sp.) is that they are surrounded (or bounded) by a cytoplasmic membrane. This membrane harbors the internal contents of the cell and regulates the movement of substances into and out of the cell. Only those molecules that can diffuse across the membrane or are transported across it can move into and out of the cell. Some molecules can pass through the lipid core of the membrane but other molecules must pass through membrane pores. Still other molecules must cross the membrane attached to carriers in an energy dependent manner. Likewise, the nucleus and other cellular organelles have membranes to regulate the flow of molecules into and out of those organelles.

What is needed are compositions and methods for the improved permeability of cell walls of *Mycobacterium* sp. to foreign particles such as labeled detection molecules such as nucleic acid (RNA or DNA) or peptide nucleic acid (PNA) probes with or without labeled detection moieties and methods of detecting and differentiating said *Mycobacterium* species. Furthermore, what is needed are compositions and methods for the improved detection of cellular targets and pathogens.

SUMMARY OF THE INVENTION

What is described herein are, in particular, compositions and methods for the improved detection (and differentiation) of species (by, for example, detection of nucleic acids) of the *Mycobacterium* genus of microorganisms, including but not limited to *M. tuberculosis, M. avuim* complex (MAC), *M. abscessus, M. gordonae, M. fortuitum, M. kansasfi, M. malmoense, M. chelonei, M. simiae, M. senegalese, M. scofulaceum* and *M. xenopi*. Recently, Shah and Weltman described improved methods for permeabilizing cells and, in particular, *Mycobacterium tuberculosis* (U.S. patent application Ser. No. 11/494,430, which is herein incorporated by reference). Until the conceptual reduction to practice of the present invention it was unknown in the art if the methods disclosed in U.S. patent application Ser. No. 11/494,430 by the same inventive entity as the present invention would be effective on all species of *Mycobacterium*. Furthermore, it was unknown in the art at the time of the constructive reduction to practice of the present invention if the various species of *Mycobacte-*

*rium* could be identified and differentiated using the compositions and methods disclosed herein.

In one embodiment, the invention allows detection of a suspected target or target fragment (e.g., DNA, RNA or PNA specific to a particular organism), directly from cells in a cell culture or specimen obtained from a patient, by, for example, in situ hybridization. In a preferred embodiment, the cell is a *Mycobacterium* sp. cell, *M. tuberculosis* or *M. avium* complex (MAC) microorganisms. The method is comprised of several steps that are performed, preferably, but not necessarily, in the listed order. A sample of the culture or specimen is deposited, for example, onto a slide. The sample is fixed onto the slide either by heat or with a standard fixative or transferred to the slide in a fixative solution so that the transfer and fixation are concurrent. The fixative can be, for example, methanol, methanol acetic acid, acetone, formaldehyde or formalin. The fixed sample is treated with IDF solutions (described by Shah and Weltman, U.S. patent application Ser. No. 11/494,430, which is herein incorporated by reference in its entirety) and variations below, stained or probed and observed.

Alternatively, the specimen (after pretreatment to solubilize the matrix and/or concentration of the specimen by centrifugation or filtration, for example) is mixed with IDF solution, incubated, then smeared or otherwise placed onto a glass slide, air-dried and fixed. The IDF solution can comprise, for example, any combination of the following reagents: chaotropic salts (e.g., guanidine thiocyanate or guanidine hydrochloride), ionic detergents (e.g., SDS) and/or non-ionic detergents (e.g., IPGEL, deoxycholate, cholate or bile salts) or other reagents with similar properties, methanol and acetic acid. The concentration of each reagent in the IDF solution depends, for example, on the cell wall of the pathogen to be detected. Detailed, preferred embodiments of the methods of the present invention are given in the Experimental section, Infra.

Although the present invention is not limited by any theory or mechanism, it is believed that the IDF solution makes "channels" in the cell wall and/or membranes (cellular and nuclear) of the pathogen. These channels allow a probe to penetrate the cell wall and cell membrane and enter the cytoplasm and/or the nucleus of the pathogen.

A probe or probes useful in the present invention may comprise, for example, DNA, RNA, PNA, peptide, glycopeptide, lipoprotein, or glycolipid or a mixture of any of the above. The targets of the fixed cells in the sample are contacted with a probe complex specific for the target(s) under conditions appropriate for hybridization or binding (for example, as described in U.S. Pat. No. 6,165,723 to Shah and Harris, which is incorporated herein by reference in its entirety). Non-hybridized or non-bound probe may then be rinsed from the sample. In one embodiment, the rinsed sample may then be stained with an appropriate counterstain (e.g., Evans Blue, DAPI, potassium permanganate, etc).

The hybridized or bound probe complex is visually detected by, for example, microscopy or flow cytometry (fluorescence activated cell sorting—FACS), with the presence of the probe complex being an indication of the presence of the cell target. The method can be performed with different hybridization buffers, several non-limiting examples of which are disclosed herein and in U.S. Pat. No. 6,165,723 to Shah and Harris, which is incorporated herein by reference in its entirety. The hybridization buffer used is determined by the nature of the probe used. The method of the present invention is useful for detecting cells, cell constituents and, preferably, pathogens in a specimen. Exemplary, non-limiting specific probe complexes are disclosed herein that are useful, for example, for detecting pathogens of the genus *Mycobacterium*; detecting and differentiating *M. tuberculosis* complex (MTB Complex) from *Mycobacterium* other than *M. tuberculosis* complex (MOTTS) and detecting and differentiating *M. avium* complex (MAC) bacteria from non-avium complex *Mycobacterium*.

The methods of the present invention are useful, for example, in detecting nucleic acids, peptides, glycopeptides, lipopeptides and glycolipids from a wide variety of specimens. Specimens include, for example, cells, cell types, tissues or a pathogen or pathogens of interest including or derived from, e.g., serum, plasma, sputum, bronchial alveolar lavage, urine, cerebral spinal fluids, tissues, semen and breast milk. The compositions and methods of the present invention may be used on specimens from any organism including, but not limited to, mammals, reptiles, fish, birds (aves), plants and insects.

In one embodiment, the present invention contemplates a composition (IDF solution) for increasing the permeability of cell walls, cell membranes, organelle membranes and nuclear membranes, said composition comprising in one embodiment: GuSCN (guanidine thiocyanate), Tris-HCL, EDTA, IGEPAL (octylphenoxy poly(ethyleneoxy)ethanol), acetic acid, methanol, sodium cholate and sodium deoxycholate. The present invention further contemplates that the GuSCN is at a concentration of approximately 0.5 to 4.5M; the Tris-HCL is at a concentration of approximately 10 to 100 mM; the Tris-HCL is at a pH of approximately 7.0 to 9.0; the EDTA is at a concentration of approximately 0.05 to 5.0 mM; the IGEPAL is at a concentration of approximately 0.1 to 2.0 percent; the acetic acid is at a concentration of approximately 1.0 to 20.0 percent; the methanol is at a concentration of approximately 1 to 50 percent; the sodium cholate is at a concentration of approximately 0.01 to 1.25 percent and the sodium deoxycholate are at a concentration of approximately 0.01 to 1.25 percent. All percents are v/v.

The IDF solution of the present invention may be used at a 1× concentration or dilutions thereof. In a preferred embodiment, the 1× concentration of the IDF solution of the present invention comprises about 4.3 M GuSCN, about 0.14% sodium cholate, about 0.14% sodium deoxycholate, about 14% Acetic Acid, about 86 mM Tris-HCL at a pH of about 7.8, EDTA at about 3 mM and IGEPAL at about 0.8%. Methanol may be added to the solution while maintaining the concentrations of the other ingredients as given or the solution may be used to permeabilize specimens (samples) that have already been fixed. Methanol may be added at a concentration ranging from 1 to 50% of the total volume.

Depending on the sample, the IDF solution of the present invention may be used at dilutions of the formulation given above. For example, the IDF solution of the present invention may be used at 0.5×, 0.3×, 0.2× or 0.1× or any other dilution from 0.99× to 0.05× of the formulation given above. Dilutions may be made with water and/or methanol. One skilled in the art will be able to determine the correct concentration of IDF solution for use with any particular specimen or sample not listed without undue experimentation by running simple concentration curve experiments. Table 1, below, gives exemplary dilutions depending on the cell types used when the IDF solution is used prior to probe hybridization. Table 2, below, gives exemplary dilution ranges for sample pretreatment before preparing a smear. Smears may also be prepared and then treated with the IDF solution of the present invention at a concentration of approximately 0.5×.

TABLE 1

Culture Smears fixed in methanol

| Cel Types | Conc of IDF for Treatment Prior to Hybridization |
|---|---|
| M tuberculosis Complex (MTB) | 0.5 to 1x IDF |
| M. avium Complex (MAC) | 0.5x IDF |
| M. abscesses | 0.5x IDF |
| M. chelonae | 0.5x IDF |
| M. gordonae | 0.5x IDF |
| M. kansasii | 0.5x IDF |
| Mucogenic Mycobacteria | No IDF |
| M. fortuitum | 0.1 to 0.5x IDF |

TABLE 2

| Clinical Sample or Spiked Sputum with | Dilution of IDF Solution (0.1x, 0.2x, etc) for Pretreatment Before Preparing Smear |
|---|---|
| M. tuberculosis Complex (MTB) | Between 0.50x to 1.00x |
| M. avium Complex (MAC) | Between 0.10x to 0.30x |
| M. kansasii | Between 0.10x to 0.20x |
| M. abscesses | Between 0.10x to 0.20x |
| M. gordonae | Between 0.15x to 0.25x |
| M. scrofulacium | Between 0.15x to 0.20x |
| M. xenopi | Between 0.10x to 0.20x |

In another embodiment GuSCN buffer is replaced with GuHCL buffer of between about 2M to 6M. In still another embodiment IGEPAL is replaced with SDS about 0.01% to 2.0%. In yet still another embodiment GuSCN is used in conjunction with GuHCL and/or IGEPAL is used in conjunction with SDS.

In one embodiment, the present invention contemplates a method for staining a target in a cell, comprising: a) contacting the cell with a composition comprising GuSCN (guanidine thiocyanate) or GuHCL (guanidine hydrochloride) or mixture of GuSCN and GuHCL, Tris-HCL, EDTA, IGEPAL (octylphenoxy poly(ethyleneoxy)ethanol), acetic acid, methanol and sodium deoxycholate to create a permeabilized cell; b) contacting the permeabilized cell of step (a) with a binding agent specific for binding to said target and; c) detecting said binding agent of step (b) by methods known in the art such as microscopy, PCR, RT-PCR, flow cytometry, etc.

In other aspects, the invention contemplates that the target of the above method is selected from, for example, nucleic acids, peptides, glycoproteins, lipids and lipoproteins of, for example, Mycobacterium sp., gram positive and gram negative bacteria, viruses, prions and mycoplasma.

In other embodiments, the present invention contemplates that the binding agent is selected from a group consisting of nucleic acids, peptide nucleic acids, peptides, lipoproteins, glycoproteins, antibodies or antibody fragments and lipids.

The binding agent of the present invention may additionally comprise a detection moiety and the detection moiety may be selected from a group comprising, for example, fluorescent markers, radioactive markers, dyes, colloidal metals, biotin/avidin, horseradish peroxidase, etc. In one preferred embodiment, the detection is via a labeled antibody with affinity for the target antigen. A binding agent comprising a detection moiety is defined herein as a probe complex.

In one embodiment, a clinical sample is treated with IDF solution in the tube, followed by boiling to release nucleic acid in solution. This technique is effective for targets such as Mycobacterium, fungi and yeasts that require mechanical lysis (e.g., by sonication) or long incubations with enzymes to digest the cell walls, for example. The target of interest can be further purified by (1) standard DNA purification techniques or (2) by sandwich hybridization using specific probes. The purified target DNA and RNA can then be amplified by PCR or RT-PCR respectively, if necessary, prior to detection.

In a more preferred embodiment, the target is a nucleic acid from the microorganism from Genus Mycobacterium and the binding agent is an oligonucleotide (or PNA probe) complementary to nucleic acids from a microorganism of Mycobacterium sp.

In a more preferred embodiment, the target is a nucleic acid from the microorganism from Mycobacterium tuberculosis or from Mycobacterium tuberculosis complex (MTB Complex) and the binding agent is an oligonucleotide (or PNA probe) complementary to nucleic acids from the microorganism Mycobacterium tuberculosis.

In a more preferred embodiment, the target is a nucleic acid from the microorganism from Mycobacterium avium complex (MAC; including M. avium, M. intracellulaire or M. scrofulaceum) and the binding agent is an oligonucleotide (or PNA probe) complementary to nucleic acids from the microorganism Mycobacterium avium complex organisms.

In another aspect, the method also comprises background staining to better highlight or visualize the detection moiety. Background stains and staining techniques are known to those practiced in the art and described in greater detail herein.

DETAILED DESCRIPTION OF THE INVENTION

The present invention is based on the discovery of an improved method of allowing the probe to penetrate the cell wall of microorganisms of the genus Mycobacterium including but not limited to M. tuberculosis complex (MTB Complex), M. avium complex (MAC) for directly detecting the presence of a target nucleic acid, protein, peptide, lipopeptide, glycopeptide, lipid, etc., in cells from culture or from specimens obtained from an individual (e.g., sputum, biopsies, CSF, paraffin embedded tissues) by in situ hybridization. The invented method is particularly well suited for detecting nucleotide sequences specific to pathogens that which are found within, for example, sputum, whole blood, central spinal fluid (CSF), other body fluids or infected tissues. More specifically, novel improvements of the traditional fixation/ pretreatment methods are described that allow probes (e.g., oligonucleotide probes, PNA probes or antibodies and antibody fragments) to penetrate inside cells (e.g., pathogens such as bacteria, viruses, fungi, yeast and protozoans), which may be located either inside or outside infected host cells. In addition, a procedure with a counterstain (e.g., DAPI, Evans Blue, potassium permanganate) after hybridization with a fluorescence labeled probe, for example, allows the organisms that retain the hybridized probes to be easily visualized in culture or clinical samples.

The novel and unique in situ hybridization pretreatment procedures, detection techniques and compositions of the present invention described herein allow the use of recombinant DNA, RNA or DNA and RNA oligonucleotides, PNA, peptide, glycoproteins (including antibodies and antibody fragments), lipids and glycolipid probes in cells, microorganisms or tissue sections and is compatible with microscopic examination routinely performed in bacteriology, parasitology, histology or pathology laboratories. For example, the present invention applies a nucleic acid probe of predetermined nucleotide sequence to the sample cells (or tissue) and to the examination of the sample by, for example, microscopy, electron microscopy, flow cytometry, oligonucleotide amplification (e.g., PCR and RT-PCR) or radioactive imaging (e.g., X-ray film, phosphorimaging), to determine which cells (or tissues) within the population contain the specific targets (e.g., nucleic acid sequences) of interest or if the target is generally present in the sample. Thus, in one embodiment, in infected whole blood smears or tissue sections, pathogenic organisms such as bacteria, virus, protozoan or fungi can be detected within the infected cells. Such protocols provide useful diagnostic and scientific information since the presence or absence of a specific nucleic acid can correlate with one or more cells of observable structure and morphology, and, in this way, provide a basis for clinical diagnosis and prognosis.

The method for detecting a target nucleic acid fragment directly from a specimen is comprised of steps that are to be performed, preferably, in the order(s) listed. A specimen, usually obtained from an individual, is first deposited onto a slide. The sample is fixed onto the slide with fixative (e.g., methanol, methanol-acetic acid fixative or a formalin-acetic acid fixative). Once the sample is fixed, the sample cells are permeabilized with the compositions and methods of the present invention. Alternatively, the specimen is mixed with IDF solution in a tube, incubated and then deposited onto a slide, air dried and fixed. Next, the cells are contacted with a probe specific for the target under conditions appropriate for hybridization.

After an adequate period of hybridization any non-hybridized probe is rinsed from the sample. In a preferred embodiment, the sample is then contacted with a counterstain (e.g., DAPI, Evans Blue, Potassium permanganate, etc.). Regardless if the sample was counterstained, probes that are hybridized to the target of the sample are then visually (or otherwise) detected by, for example, microscopy. The presence of probe within the sample is an indication of the presence of the target fragment. Counterstaining the sample concurrently or sequentially with the in situ hybridization assay of the present invention enhances the method by allowing, for example, a clearer determination of the location of the target within the sample. Such information helps, for example, to provide a clearer determination of background hybridization.

This method is suitable for use with any specimen obtained from an individual. This includes, without limitation, whole blood, serum, plasma, sputum, urine, breast milk, semen, cerebral spinal fluid and tissue. This method is also suitable for detection of a pathogen or other target within the cells of an insect vector, insect cell, plant cells, fungi and bacteria.

The purpose of fixing cells or tissue is to immobilize the cells and to preserve the morphology of the cells or tissue so cell constituents such as, for example, RNA are retained within the cellular matrix during in situ hybridization. The preferred method thus utilizes a fixative which is able to preserve and retain nucleic acids of the cell and at the same time cross-link and/or precipitate the proteins in the cellular matrix such that the cell or tissue remains substantially in open configuration for probe penetration and subsequent hybridization.

In a preferred embodiment, the probes of the present invention comprise, for example, synthetic or biologically produced nucleic acids (DNA, RNA and equivalents); peptide nucleic acids (PNA; and equivalents); peptides (and equivalents) that contain specific nucleic acid or peptide sequences which hybridize under stringent conditions to specific cellular targets. In another embodiment, the probes of the present invention comprise synthetic or biologically produced glycopeptides, lipopeptides and prions or prion-like molecules (or the equivalents thereof) that bind under stringent conditions to specific targets within the cell.

The probe complex is defined as a probe that comprises a marker moiety suitable for detection. If the probe is a nucleic acid, the marker moiety is attached at either the 5' end, the 3' end, internally, or in any combination thereof. The preferred marker moiety is an identifying label such as radiolabel (e.g., $P^{32}$, $I^{125}$, $H^3$), a biotin label or a fluorescent label. Alternatively, the probe has a labeled poly-deoxynucleotide tail that is used for detection of the probe complex. The probe complex may also be comprised of a plurality of different nucleic acid sequences, PNA, peptides, glycopeptides, lipopeptides or prions or any combination thereof comprising one or more labeled with a marker moiety. If more than one of the probe moieties are labeled it may be beneficial to label the each of the probe moieties with a different marker moiety.

The nucleotide sequence of an oligonucleotide probe or PNA probe is substantially complementary to at least a portion of the target nucleic acid. The target nucleic acid is either a nucleic acid normally present within the fixed cell or tissue or, alternatively, that is not normally present in the cell or tissue and is associated with an abnormal or pathological state. Each probe complex molecule is preferably comprised of a DNA or RNA fragment ranging in size from about 10-50 nucleotides.

Peptide probes include, for example, antibodies and other molecules known to be capable of binding a defined target or range of targets. Examples of non-antibody probes included, for example, enzymes and enzyme substrates and the effecter portions thereof. Additionally, known drugs or chemicals may selectively bind target proteins (e.g., antibiotics may bind bacteria). Lipopeptides, for example, are useful for the detection of lipid moieties in a cell including specific organelles or portions of organelles and bacteria internalized in a cell. Glycopeptides, for example, interfere with platelet aggregation and, therefore, may be used to target molecules necessary in platelet function thereby aiding in research and diagnosis of clotting abnormalities. Prions, or portions thereof may be used, for example, as probes for neurological tissues. Likewise, prions may be targets in fixed samples.

In a preferred embodiment, the probe is added to the sample in excess of the target (e.g., 10:1, 100:1 or 1000:1). This is to drive the hybridization reaction efficiently and to promote a high rate of probe:target binding.

The probe complex (comprising, for example, DNA, RNA and or PNA) is contacted with the target (e.g., nucleic acids) of the sample, generally by contacting the sample with the probe complex. Exemplary conditions appropriate for hybridization are solutions that provide the appropriate buffered environment. Some examples of appropriate hybridization buffers are:

1) a buffer comprising between about 10% and 50% formamide, 2×.SSC (pH 7.4), and 1% NP40;
2) a buffer comprising between about 1.5 M and 4 M GuSCN buffer;
   5 M GuSCN stock buffer is made from 5 M GuSCN, 100 mM Tris-HCl (pH 7.8), 40 mM EDTA, 1% NP40. This stock buffer is diluted to the indicted molarity of GuSCN by the addition of 1×TE (Tris/Tris-HCl 10 mM, EDTA 1 mM) to produce the above referenced GuSCN buffer molarities.
3) a buffer comprising between 2 to 6 M GuHCl buffer.
   8 M GuHCl stock buffer is made from 8 M GuHCl, 200 mM Tris-HCl (pH 7.8), 40 mM EDTA, 1% NP40. This stock buffer is diluted to the indicated molarity of GuHCl by the addition of 1×TE (pH 7.8) to produce the above referenced GuHCl buffer molarities.
4) a buffer comprising of a mixture of formamide (20-50%) and GuSCN buffer. (e.g., 0.5M to 3M).

5) a buffer comprising of a mixture of GuSCN buffer (e.g., 0.5M to 3M) and GuHCL buffer (e.g., 1M to 5M).

The specific composition and concentration of hybridization buffer varies with the type of probe or probe complex used. The composition and concentration of buffer used is, also, dependent on the Tm (melting point: the temperature at which double stranded DNA separates forming two complementary single strands) of the probe, probe sequence, probe length and hybridization temperature and can be determined by one of skill in the art through the course of no more than routine experimentation.

The present invention is not limited to any particular hybridization temperature. However, it should be appreciated that the use of formamide in the hybridization buffer allows hybridization to be carried out at a much lower temperature than standard hybridization protocols. For example, hybridization of an average probe complex specifically to the target (and not to host cells) in aqueous hybridization buffer such as sodium chloride would generally require a temperature of about 60-65° C. The same hybridization performed at about 42° C. in hybridization fluid 1) above, would provide equivalent specificity.

Likewise, the use of GuSCN or GuHCl also allows hybridization to be carried out at a much lower temperature than standard hybridization protocols. For example, in an average procedure, hybridization of the probe specifically to the target (and not to host cells) in aqueous hybridization buffer such as sodium chloride would require temperatures of approximately 60-65° C. However, the same hybridization performed in the GuSCN or GuHCl hybridization buffer above, at about 37° C. (or ~25° C.) will provide equivalent specificity of hybridization.

After hybridization is complete, the non-hybridized probe is rinsed from the sample, generally by applying a series of washes with a wash buffer. It is within the means of those skilled in the art to determine appropriate wash buffers and wash times. In one embodiment, the wash buffer comprises 0.3 M sodium chloride, 0.03 M sodium citrate, and 0.1% SDS. Another appropriate wash buffer comprises phosphate buffered saline (PBS).

After rinsing, the sample may be counterstained. In one embodiment, counterstaining of the background enhances the visualization of the hybridized probes. Preferred counterstains are, for example, DAPI, Evans Blue and potassium permanganate. Other appropriate counterstains are known by those practiced in the art. This staining step is generally applied when a fluorescent-labeled probe is used to detect nucleic acids, proteins, glycoproteins and lipoproteins that are specific for a target. Although helpful, the counterstains are not required for the embodiments of the present invention.

The probe is detected by means suitable for the specific moiety used to label the probe complex. The preferred method for detecting fluorescent-labeled probes, for example, employs special green, red and blue microscope filters (i.e., fluorescent microscopy). Hybridized radiolabeled probes can be detected by, for example, autoradiography and phosphorimaging. Biotin labeled probes can be detected by enzymatic detection systems and such detection systems are commercially available.

The method described above allows for the simultaneous detection of different pathogens in a single clinical sample by performing one reaction with a probe complex that is comprised of a plurality of different nucleic acid sequences, each labeled with a different marker moiety. For simultaneous detection the different oligonucleotide probes, which are specific for the different nucleic acids of the different targets commonly present in the specimen, they can be designed such that the Tm (melting point) values of all the probe complex sequences are very similar. Each specific oligonucleotide is then labeled with a different detectable moiety (e.g., different fluorescent moieties). Hybridization is performed with the multiple components of the probe complex. The hybridized sample is processed as described above and the sample is observed by means appropriate for detection of the different labeled oligonucleotides of the probe complex (e.g., viewed using appropriate filters if different fluorescent moieties are used) to detect which of the targets is present in the sample.

It will be recognized by practitioners ordinarily skilled in this art that the novel pretreatment protocol for use with the in situ hybridization protocol described herein is compatible with all previously known methods of detection as well as the ones described herein and is not limited by the method of detection used. The in situ hybridization protocol has been streamlined so that fewer manipulations are necessary and can therefore be performed in a short time. Embodiments of the present invention also encompass kits comprising the compositions of the present invention and instructions for use. Such compositions when provided in a kit form will allow the practice of various embodiments of the protocols presented herein including those that have been optimized for simplicity and for compatibility with a wide variety of detection methods. It is also expected that such prepared kits containing specifically prepared reagents and probes will be applicable in clinical/diagnostic laboratories, where the ability to detect the presence or absence of specific nucleic acids would serve to positively or negatively identify pathological states characterized by the presence of specific targets.

The available diagnostic methods of the prior art for many cellular pathologies depends on microscopic evaluations, cellular morphological parameters, staining characteristics, and the presence or absence of certain targets. However, many of these diagnostic methods are not entirely accurate or sufficiently sensitive. In situ hybridization using the above described protocol and pathogen specific probes will allow easier and more accurate identification of targets (including, but not limited to, pathogens) in samples.

The present invention provides a simple pretreatment protocol for use in in situ hybridization protocol that provides enhanced probe penetration into cells and, thus, improves hybridization and detection characteristics as compared to previously described protocols. The improvements include maximizing the sensitivity of the assay by increasing efficiency of hybridization and detection of specific "signal." Although the present invention is not limited to any particular mechanism, it is believed that the increased sensitivity is due to improved hybridization due to improved probe penetration into the cells and, at the same time, maximized retention of the target (e.g., nucleic acid sequences) in the cell or tissue and, maximizing preservation of the other biochemical and morphological characteristics of the cell or tissue sample.

EXPERIMENTAL

A preferred and non-limiting use of the above method is in the detection of *Mycobacterium*, and speciation of *Mycobacterium* tuberculosis, and *M. avium* complex (MAC; *M. avium*, *M. scrofulaceum* and *M. intracellaire*) from a culture or from sputum. It will be understood and appreciated by one of skill in the art that the novel methodology is equally applicable to a wide variety of other systems, cells, tissue cultures and tissues for hybridization of specific nucleic acids (or detection of other cellular components of the target cells, tissues or pathogens) of interest with concomitant preservation of cell integrity and morphology.

Example 1

Sample Preparation

The present invention contemplates a composition (IDF solution) for increasing the permeability of cell walls, cell membranes, organelle membranes and nuclear membranes, said composition comprising in one embodiment: GuSCN (guanidine thiocyanate), Tris-HCL, EDTA, IGEPAL (octylphenoxy poly(ethyleneoxy)ethanol), acetic acid, methanol, sodium cholate and sodium deoxycholate. The present invention further contemplates that the GuSCN is at a concentration of approximately 0.5 to 4.5 M or GuHCL at a concentration of 1M to 7.5M or a mixture of GuSCN and GuHCL; the Tris-HCL is at a concentration of approximately 10 to 100 mM; the Tris-HCL is at a pH of approximately 7.0 to 9.0; the EDTA is at a concentration of approximately 5 to 50 mM; the IGEPAL is at a concentration of approximately 0.1 to 2.0 percent; the acetic acid is at a concentration of approximately 1.0 to 20.0 percent; the methanol is at a concentration of approximately 0.1 to 50 percent; the sodium cholate is at a concentration of approximately 0.01 to 1.25 percent and the sodium deoxycholate is at a concentration of approximately 0.01 to 1.25 percent.

*Mycobacterium* Culture Samples

Sample Preparation Method 1a

Smears were prepared from cultures of the Mycobacterial species as described below. Briefly, for example, an aliquot of cell culture, resuspended in distilled water, was smeared onto a glass slide and air-dried, fixed with methanol or methanol:acetic acid or ethanol. The fixed smear was washed with PBS three times (or distilled water) prior to hybridization.

Sample Preparation Method 1b

Smears were prepared from cultures of the Mycobacterial species as described below. Briefly, for example, an aliquot of cell culture was smeared onto a glass slide and air-dried, fixed with methanol or methanol:acetic acid or ethanol. The fixed smear was treated with IDF solution for about 5 minutes, prior to hybridization. Before hybridization the slide was washed with PBS (or distilled water) three times.

Clinical Samples or Spiked Sputum Samples

Sample Preparation Method 2a For example, one volume of a patient's unprocessed sputum was mixed with about 0.2-0.5 volumes of IDF solution (as disclosed, Supra) in a tube and incubated at room temperature (about 20-25° C.) for about 15 minutes. The sputum-IDF mixture was then smeared onto a glass slide, air dried and fixed with methanol or equivalent. The IDF treatment of the fixed smear prior to hybridization was omitted. Before hybridization the slide was washed with PBS (or distilled water) three times.

Sample Preparation Method 2b

One volume of a patient's unprocessed sputum was mixed with 0.2 to 1.0 volumes of IDF solution (Supra) in a tube and incubated at room temperature (about 20-25° C.) for about 15 minutes. The sputum-IDF mixture was then smeared onto a glass slide, air dried and fixed with methanol or equivalent. The fixed smear was treated with IDF solution for 10 minutes, prior to hybridization. Before hybridization the slide was washed with PBS (or distilled water) three times.

Sample Preparation Method 3a

Briefly, for example, either clinical sputum samples or Mycobacterial cell culture, spiked into pooled *Mycobacterium* negative sputum was treated with DTT or Nalc to liquefy the sputum. IDF solution (about 0.2 to 1 volume) was added to the treated sputum, mixed thoroughly by, for example, vortexing and incubated at room temperature (about 20-25° C.) for about 15 minutes. The IDF treated sputum sample was then smeared onto a glass slide and air-dried. The sample was fixed by methanol or methanol-acetic acid or ethanol.

Sample Preparation Method 3b

Briefly, either clinical sputum samples or Mycobacterial cell culture, spiked into pooled *Mycobacterium* negative sputum was treated with DTT or Nalc to liquefy the sputum. IDF solution (about 0.2 to 1 volume) was added to the treated sputum, mixed thoroughly by, for example, vortexing and incubated at room temperature (about 20-25° C.) for about 15 minutes. The IDF treated sputum sample is then smeared onto a glass slide and air-dried. The sample was fixed by methanol or methanol-acetic acid or ethanol. The fixed smears were treated with the IDF solution (as disclosed, Supra) for about 5 minutes. After IDF treatment the smear was washed 3 times with PBS (or distilled water) and air-dried.

Processed Sputum or other Clinical Sample Pellets

Sample Preparation Method 4a Sputum was processed by NALC/NaOH. Briefly, for example, about one volume of NALC/NaOH solution (a chaotropic solution such as guanidine hydrochloride or thiosulphate may be used in place of Nalc/NaOH) was added to sputum and mixed thoroughly by, for example, vortexing. The sample was incubated at room temperature (about 20-25° C.) for about 20 minutes and then neutralized with phosphate buffer, pH 6.8. The sample was centrifuged to pellet the cells. The cells were washed with phosphate buffered saline. Washed cells were suspended in phosphate buffered saline with 1% BSA. The prepared sputum sample was then smeared onto a glass slide and air-dried. The sample was fixed by methanol or methanol-acetic acid or ethanol. The fixed smear was treated with the IDF solution (Supra) for about 5 minutes. After 5 minutes the smear was washed 3 times with PBS (or distilled water) and air-dried.

Sample Preparation Method 4b

Sputum was processed by either 1) NALC/NaOH or 2) with a chaotropic solution such as guanidine hydrochloride or thiosulphate. Briefly, for example, one volume of Nalc/NaOH solution was added to sputum and mixed by vortexing. The sample was incubated at room temperature (about 20-25° C.) for about 20 minutes and then neutralized with phosphate buffer, pH 6.8. The sample was centrifuged to pellet the cells. The cells were washed with phosphate buffered saline. Washed cells were suspended in phosphate buffered saline with 1% BSA. To one volume of washed cells, between about 0.2 to 0.5 volumes of IDF solution was added and incubated at room temperature for about 15 minutes. The IDF treated processed sputum sample was then smeared onto a glass slide and air-dried. The sample was fixed by methanol or methanol-acetic acid or ethanol.

Sample Preparation Method 5

One volume of a patient's unprocessed sputum was mixed with about 0.2 to one volume of IDF solution (Supra) in a tube and incubated at about 20-25° C. (ambient temperature) for about 15 minutes. The sputum—IDF mixture was boiled for approximately 15 minutes to release nucleic acids in solution and at the same time render the sample non-infectious. Nucleic acids can be purified by standard techniques from the boiled sample or the target nucleic acid of interest can be selected by sandwich hybridization using specific probes and magnetic beads as described by Shah, et al. (U.S. Pat. No. 5,629,156, which is incorporated herein by reference). The purified target was amplified by PCR (for a DNA target) or RT-PCR (for an RNA target).

Example 2

Probing of Samples

*Mycobacterium* sp. Probes

An oligonucleotide or peptide nucleic acid probe comprised of a DNA sequence that specifically hybridizes to: 16S ribosomal RNA of all species of *Mycobacterium* are preferably used in the detection of the presence of *Mycobacterium* in culture, spiked samples and clinical samples. One non-limiting example of a suitable *Mycobacterium* genus probe for use, for example, in a FISH assay is:

[SEQ. ID NO.: 1]
5'-ATCGCCCGCACGCTCACAGTTAAGCCGTGAGATTTC-3'.

(U.S. Pat. No. 5,521,300, to Shah, et al., 1996 and incorporated herein by reference). SEQ. ID NO: 1 and the complements thereof are suitable for detection of *Mycobacterium* sp. In another embodiment, an RNA molecule of the same sequence as SEQ ID NO.: 1, except wherein the thymine residues are replaced with uracil residues, may also be used as may a comparable PNA sequence.

*Mycobacterium tuberculosis* (MBT) Probes

23 S ribosomal RNA of *Mycobacterium tuberculosis* were preferably used as probes in the detection of the presence of *M. tuberculosis* in cells. One non-limiting example of a suitable probe complex for use in, for example, a FISH assay is:

[SEQ. ID NO.: 2]
5'-GAACACGCCACTATTCACACGCGHGCTATGCGTGTGGGTCGCCCTAT

TCAG-3'.

(U.S. Pat. No. 5,521,300, to Shah, et al., 1996 and incorporated herein by reference). SEQ. ID NO: 2 and the complements thereof, are suitable for detection of *M. tuberculosis*. In another embodiment, an RNA molecule of the same sequence as SEQ ID NO.: 2, except wherein the thymine residues are replaced with uracil residues, may also be used as may a comparable PNA sequence.

*M. avium* Complex (MAC) Probe Mix 16S and 23S ribosomal RNA of *Mycobacterium avium* complex are preferably used in the detection of the presence of *M. avium* complex (MAC: *M. avium*, *M. intracellulaire* and *M. scrofulaceum*) in culture, clinical samples or spiked samples of cells. Examples of a suitable probe complex mix for use, for example, in a FISH assay, are:

[SEQ. ID NO.: 3]
5'- TGC-GTC-TTG-AGG-TCC-TAT-CC -3'.

[SEQ. ID NO.: 4]
5'- TGT-CCA-TGC-ATG-CGG-TTT-3'.

[SEQ. ID NO.: 5]
5'- ACG-CCA-CTA-CAC-CCC-AAA-3'.

SEQ. ID NOs.: 3, 4 and 5 are suitable, for example, for the detection of *M. avium* complex (MAC; *M. avium*, *M. intracellulaire* and *M. scrofulaceum* species). In another embodiment, an RNA molecule of the same sequences as SEQ ID NOs.: 3, 4 and 5, except wherein the thymine residues are replaced with uracil residues, may also be used as may a comparable PNA sequence.

Example 3

MTB and MAC FISH Assays

Probe SEQ. ID NO.: 2 and a probe set comprising SEQ. ID NOs.: 3, 4 and 5. Probe SEQ. ID NO.: 2 was labeled with one fluorescent dye (e.g., Tamra) and probes SEQ. ID NOs.: 3, 4 and 5 (used as a probe set) were labeled with another fluorescent dye (e.g., fluorescein (for example, fluorescein isothiocyanate: FITC)).

Results:

M-Genus FISH Assay: All the mycobacterium species—*M. avium*, *M. scrofulaceum*, *M. abscessus*, *M. gordonae*, *M. fortuitum*, *M. kansasii*, *M. malmoense*, *M. chelonei*, *M. simiae*, *M. senegalese*, *M. tuberculosis* and *M. xenopi* cultures and spiked sputum samples were positive (i.e., detected) by the M-Genus assay using SEQ. ID NO.: 1 as the probe.

MTB FISH Assay: *M. tuberculosis* cultures, smear positive clinical samples and spiked sputum samples were also positive (i.e., detected) by the MTB FISH assay, but negative (i.e., not detected) by the MAC FISH assay. All other Mycobacterial species: *M. avium*, *M. scrofulaceum*, *M. abscessus*, *M. gordonae*, *M. fortuitum*, *M. kansasii*, *M. malmoense*, *M. chelonei*, *M. simiae*, *M. senegalese* and *M. xenopi* cultures and spiked sputum samples were negative.

MAC FISH Assay: *M. avium* and *M. scofulaceum* cultures, smear positive clinical samples and spiked sputum samples were positive by *M. avium* complex FISH assay. All other Mycobacterial species, *M. tuberculosis*, *M. abscessus*, *M. gordonae*, *M. fortuitum*, *M. kansasii*, *M. malmoense*, *M. chelonei*, *M. simiae*, *M. senegalese* and *M. xenopi* cultures and spiked sputum samples were negative.

MTB-MAC FISH Assay: The *M. tuberculosis* culture, clinical samples and spiked samples gave a positive signal with the MTB probe (SEQ. ID NO.: 2) but gave no signal with the MAC probe set (SEQ. ID NOs.: 3, 4 and 5). *M. avium* and *M. scrofulaceum* gave a positive signal to the MAC probe set (SEQ. ID NOs.: 3, 4 and 5) but gave no signal to the MTB probe (SEQ. ID NO.: 2). All other Mycobacterial species, *M. abscessus*, *M. gordonae*, *M. fortuitum*, *M. kansasii*, *M. malmoense*, *M. chelonei*, *M. simiae*, *M. senegalese* and *M. xenopi* cultures and spiked sputum samples gave no signal to either the MTB probe or the MAC probes.

Methods:

The ribosomal RNA sequence was chosen for use in the detection of the *Mycobacterium* pathogens because of the high abundance of rRNA in bacterial cells (1,000-10,000 copies). Preferably the oligonucleotide or PNA probe complex is a DNA with a sequence complimentary to *Mycobacterium* rRNA. The oligonucleotide is preferably labeled at the 3' and 5' end with fluorescein. It will be recognized that a RNA oligonucleotide probe can be used as well as other labels known in the art.

As discussed above, the quantity of the total probe was a predetermined amount that should exceed the estimated amount of the available rRNA believed to be within the sample (about a 100:1 ratio) in order to drive the hybridization reaction efficiently and to promote a high rate of probe:target annealing. In quantitative terms, this requires that a probe comprised of a 30-nucleotide long oligonucleotide be used in concentrations ranging from, for example, 1-10 µg/ml to produce reliable signal above background.

It should be appreciated that use of GuSCN or GuHCl or mixture of GuSCN and GuHCl also allows hybridization to be carried out at a much lower temperature than standard hybridization protocols. Hybridization of the specified probe specifically to the target (and not to host cells) in aqueous hybridization fluid such as sodium chloride would require a temperature of about 60-65° C. However, hybridization performed in the GuSCN or GuHCl hybridization buffer above, at about 20-25° C. ensures specificity.

One of the advantages of the in situ hybridization method developed by the Inventors and detailed herein is that relatively small numbers of cells may comprise a sample and large numbers of identical samples may be processed over a short period of time. The unique in situ hybridization method of the present invention is extremely simple. The methods of the present invention can also be applied to any kind of sample, including, for example and without limitation, paraffin-embedded tissue sections and acetone fixed samples.

The results of these experiments show the detection of the target (pathogen RNA or DNA) in the tested samples and no detection of the target in control samples. Detection of the target was consistently better in the samples treated with the IDF solutions of the present invention. One skilled in the art will appreciate, understand and know the IDF solutions of the present invention may be used in any situation requiring the effective entry of a probe (or other similar object) into a cell, pathogen (e.g., located in a cell) or organelle without undue experimentation.

It should be evident from the forging that the present invention provides compositions and methods for increasing the permeability of cells, cell walls, cell membranes, organelles and organelle membranes to aid, for example, in the detection of cellular components and/or pathogens.

The invention claimed is:

1. A method for detecting *Mycobacterium* sp., comprising:
   a) providing a sample suspected of comprising *Mycobacterium* cells;
   b) making a suspension of the cells in said sample;
   c) permeabilizing but not lysing the cells in the cell suspension by contacting them with a composition comprising: Tris HCI at 10 to 100 mM, pH 7.0 to 9.0, EDTA at about 3 mM, IGEPAL at 0.1 to 2.0 percent v/v, acetic acid at 1.0 to 20 percent v/v, methanol at 1 to 50 percent v/v, sodium cholate at 0.01 to 1.25 percent v/v, sodium deoxycholate at 0.01 to 1.25 percent v/v and one of GuSCN (guanidine thiocyanate) at about 4.3 M or GuHCI (guanidine hydrochloride) at 2 to 6 M;
   d) contacting the permeabilized cells with a probe specific for *Mycobacterium* DNA or RNA to create bound probes; and
   e) detecting any bound probes inside the *Mycobacterium* cells.

2. The method of claim 1, wherein the detection step (e) comprises:
   a) isolating any bound probes from the sample;
   b) amplifying any DNA or RNA associated with the bound probes; and
   c) determining if any the DNA or RNA associated with the bound probes is from *Mycobacterium*.

3. The method of claim 1, wherein said steps 1(d) and 1(e) comprise fluorescent in situ hybridization (FISH).

4. The method of claim 1, wherein the method additionally comprises contacting the cells in said sample with fixative.

5. The method of claim 4, wherein the cells in said sample are contacted with fixative either following step 1b) or following step 1c).

6. The method of claim 5, wherein said cells are transferred to a slide prior to or concurrent with fixation.

7. The method of claim 1, wherein the probe comprises one or more of DNA, RNA or PNA.

8. The method of claim 1, wherein said probe comprises SEQ. ID NO.: 1.

9. The method of claim 1, wherein said probe is labeled.

10. The method of claim 1, where said sample is from a mammal, reptile, amphibian, ayes or fish.

11. The method of claim 10, wherein said sample is from a human.

12. The method of claim 1, wherein said sample is selected from a group consisting of sputum, bronchial alveolar lavage and tissue.

13. The method of claim 1, wherein said sample is concentrated by centrifugation before making the cell suspension.

14. The method of claim 12, wherein said sample is processed with NALC/NaOH, GuHCI (guanidine hydrochloride) or GuCSN (guanidine thiocyanate).

15. The method of claim 1, wherein *Mycobacterium* sp. is *Mycobacterium tuberculosis*.

16. The method of claim 15, wherein said probe comprises SEQ. ID NO.: 2.

17. A method of detecting *Mycobacterium avium* complex (MAC), comprising:
   a) providing a sample containing cells suspected of comprising one or more of *Mycobacterium avium* complex;
   b) making a suspension of the cells in said sample;
   c) permeabilizing the cells in the cell suspension by contacting them with a composition comprising: Tris-HCI at 10 to 100 mM, pH 7.0 to 9.0, EDTA at about 3 mM, IGEPAL at 0.1 to 2.0 percent v/v, acetic acid at 1.0 to 20 percent v/v, methanol at 1 to 50 percent v/v, sodium cholate at 0.01 to 1.25 percent v/v, sodium deoxycholate at 0.01 to 1.25 percent v/v and one of GuSCN (guanidine thiocyanate) at about 4.3 M or GuHCI (guanidine hydrochloride) at 2 to 6 M;
   d) contacting said permeabilized cells with probes specific for MAC wherein said probes will bind to targets in said samples if said targets are present;
   e) detecting any targets bound to said probes; and
   f) determining if MAC is present in the sample.

18. The method of claim 17, wherein said detection step 1(e) comprises:
   a) isolating any bound probes from the sample;
   b) amplifying any DNA or RNA associated with the bound probes; and
   c) determining if the DNA or RNA associated with the bound probes is from *Mycobacterium avium* complex.

19. The method of claim 17, wherein said steps 1(e) and (f) comprise fluorescent in situ hybridization (FISH).

20. The method of claim 17, wherein the method additionally comprises contacting the cells in said sample with a fixative.

21. The method of claim 20, wherein the cells in said sample are contacted with fixative either following step 1b) or following step 1c).

22. The method of claim 21, wherein said cells are transferred to a slide prior to or concurrent with fixation.

23. The method of claim 17, wherein the probes comprise one or more of DNA, RNA or PNA.

24. The method of claim 17, wherein said probes are labeled.

25. The method of claim 17, wherein said sample is from a mammal, reptile, amphibian, ayes or fish.

26. The method of claim 25, wherein said sample is from a human.

27. The method of claim 26, wherein said sample is selected from a group consisting of sputum and bronchial alveolar lavage.

28. The method of claim 17, wherein said sample is concentrated by centrifugation before making the cell suspension.

29. The method of claim 27, wherein said sample is processed with NALC/NaOH, guanidine hydrochloride or thiosulphate.

30. The method of claim 17, wherein said probes specific for MAC comprise SEQ. ID Nos.: 3, 4 and 5.

31. A method of detecting and differentiating *Mycobacterium* genus and non-MAC *Mycobacterium* from *Mycobacterium avium* complex, comprising:
   a) providing a sample containing cells suspected of comprising one or more of *Mycobacterium* sp., non-MAC *mycobacterium* or *Mycobacterium avium* complex;
   b) making a suspension of the cells in said sample;
   c) permeabilizing the cells in the cell suspension by contacting them with a composition comprising: Tris-HCI at 10 to 100 mM, pH 7.0 to 9.0, EDTA at about 3 mM, IGEPAL at 0.1 to 2.0 percent v/v, acetic acid at 1.0 to 20 percent v/v, methanol at 1 to 50 percent v/v, sodium cholate at 0.01 to 1.25 percent v/v, sodium deoxycholate at 0.01 to 1.25 percent v/v and one of GuSCN (guanidine thiocyanate) at about 4.3 M or GuHCI (guanidine hydrochloride) at 2 to 6 M;
   d) contacting said permeabilized cells with probes specific for *Mycobacterium* sp. and with probes specific for MAC said probes specific for *Mycobacterium* sp. optionally labeled with a different detection moiety than the probes specific for MAC, wherein said probes will bind to targets in said sample if said targets are present;
   e) detecting any targets bound to said probes; and
   f) determining if either non-MAC *Mycobacterium* sp. or MAC is present in the sample.

32. The method of claim 31, wherein said detection step 1(e) comprises:
   a) isolating any bound probes from the sample;
   b) amplifying any DNA or RNA associated with the bound probes; and
   c) determining if the DNA or RNA associated with the bound probes is from *Mycobacterium* sp. other than *Mycobacterium avium* complex or is from *Mycobacterium avium* complex.

33. The method of claim 31, wherein said method additionally comprises contacting the cells in said sample with fixative.

34. The method of claim 33, wherein said cells in said sample are transferred to a slide prior to or concurrent with fixation.

35. The method of claim 31, wherein the probes comprise one or more of DNA, RNA or PNA.

36. The method of claim 31, wherein said probes are labeled.

37. The method of claim 31, wherein said sample is from a mammal, reptile, amphibian, aves or fish.

38. The method of claim 37, wherein said sample is from a human.

39. The method of claim 38, wherein said sample is selected from a group consisting of sputum, tissue and bronchial alveolar lavage.

40. The method of claim 31, wherein said sample is concentrated by centrifugation before making the cell suspension.

41. The method of claim 39, wherein said sample is processed with NALC/NaOH, guanidine hydrochloride or thiosulphate.

42. The method of claim 31, wherein said steps 1(d) and 1(e) comprise fluorescent in situ hybridization (FISH).

43. The method of claim 31, wherein said probes are selected from the groups i) SEQ ID NOs.: 1, 2, 3, 4 and 5, ii) SEQ ID NOs.: 1, 3, 4 and 5, iii) SEQ ID Nos.: 2, 3 4 and 5.

44. The method of claim 31, wherein said probes specific for MAC comprises SEQ. ID Nos.: 3, 4 and 5.

45. The method of claim 1, wherein the permeabilization composition of step c) comprises: Tris-HCI at about 86 mM, pH 7.0 to 9.0, EDTA at about 3 mM, IGEPAL at about 0.8 percent v/v, acetic acid at about 14% v/v, methanol at 1 to 50 percent v/v, sodium cholate at about 0.14 percent v/v, sodium deoxycholate at about 0.14 percent v/v and one of GuSCN (guanidine thiocyanate) at about 4.3 M or GuHCI (guanidine hydrochloride) at about 4.3 M.

46. The method of claim 1, wherein said *Mycobacterium* sp. cells comprise a *Mycobacterium tuberculosis* Complex (MTB).

\* \* \* \* \*

UNITED STATES PATENT AND TRADEMARK OFFICE
CERTIFICATE OF CORRECTION

| | | |
|---|---|---|
| PATENT NO. | : 8,758,990 B2 | Page 1 of 1 |
| APPLICATION NO. | : 11/975306 | |
| DATED | : June 24, 2014 | |
| INVENTOR(S) | : Jyotsna S. Shah and Helena Weltman | |

It is certified that error appears in the above-identified patent and that said Letters Patent is hereby corrected as shown below:

In the Claims,

Column 17, claim 10, line 52-53 should read as follows:
The method of Claim 1, where said sample is from a mammal, reptile, amphibian, <u>aves</u> or fish.

Column 18, claim 25, line 53-54 should read as follows:
The method of Claim 17, wherein said sample is from a mammal, reptile, amphibian, <u>aves</u> or fish.

Signed and Sealed this
Seventh Day of October, 2014

Michelle K. Lee
*Deputy Director of the United States Patent and Trademark Office*

SEQUENCE LISTING

```
<160> NUMBER OF SEQ ID NOS: 5

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
atcgcccgca cgctcacagt taagccgtga gatttc                              36

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gaacacgcca ctattcacac gcgcgtatgc gtgtgggtcg ccctattcag               50

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgcgtcttga ggtcctatcc                                                20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgtccatgca tgcggttt                                                  18

<210> SEQ ID NO 5
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 5
acgccactac accccaaa                                                    18
```